US009938279B2

(12) United States Patent
Chen et al.

(10) Patent No.: US 9,938,279 B2
(45) Date of Patent: Apr. 10, 2018

(54) METHOD FOR TREATING DISEASE OR CONDITION SUSCEPTIBLE TO AMELIORATION BY AMPK ACTIVATORS AND COMPOUNDS OF FORMULA WHICH ARE USEFUL TO ACTIVATE AMP-ACTIVATED PROTEIN KINASE (AMPK)

(71) Applicants: Han-Min Chen, Taipei (TW); Cheng-Yi Kuo, Taipei (TW); Chun-Fang Huang, Taipei (TW); Jiun-Tsai Lin, Taipei (TW)

(72) Inventors: Han-Min Chen, Taipei (TW); Cheng-Yi Kuo, Taipei (TW); Chun-Fang Huang, Taipei (TW); Jiun-Tsai Lin, Taipei (TW)

(73) Assignee: ENERGENESIS BIOMEDICAL CO., LTD, New Taipei (TW)

( * ) Notice: Subject to any disclaimer, the term of this patent is extended or adjusted under 35 U.S.C. 154(b) by 225 days.

(21) Appl. No.: 13/858,954

(22) Filed: Apr. 9, 2013

(65) Prior Publication Data

US 2014/0303112 A1    Oct. 9, 2014

(51) Int. Cl.

| C07D 473/00 | (2006.01) |
|---|---|
| C07D 473/40 | (2006.01) |
| C07D 473/34 | (2006.01) |
| C07D 473/30 | (2006.01) |
| C07D 473/06 | (2006.01) |
| C07D 473/16 | (2006.01) |
| C07D 473/18 | (2006.01) |
| C07D 473/38 | (2006.01) |
| C07D 473/24 | (2006.01) |
| C07D 239/47 | (2006.01) |
| C07D 239/54 | (2006.01) |
| C07D 239/553 | (2006.01) |
| C07D 253/075 | (2006.01) |
| C07D 473/32 | (2006.01) |

(52) U.S. Cl.
CPC ......... *C07D 473/00* (2013.01); *C07D 239/47* (2013.01); *C07D 239/54* (2013.01); *C07D 239/553* (2013.01); *C07D 253/075* (2013.01); *C07D 473/06* (2013.01); *C07D 473/16* (2013.01); *C07D 473/18* (2013.01); *C07D 473/24* (2013.01); *C07D 473/30* (2013.01); *C07D 473/32* (2013.01); *C07D 473/34* (2013.01); *C07D 473/38* (2013.01); *C07D 473/40* (2013.01)

(58) Field of Classification Search
CPC .. C07D 473/00; C07D 473/32; C07D 239/54; C07D 473/40; C07D 473/34; C07D 473/30; C07D 473/06; C07D 473/16; C07D 473/18; C07D 239/47; C07D 239/553; C07D 253/075; C07H 19/06; C07H 19/052

USPC ......... 514/263.4, 274, 263.1, 263.3, 263.34, 514/263.37, 242, 43, 50
See application file for complete search history.

(56) References Cited

U.S. PATENT DOCUMENTS

| 6,838,469 | B2* | 1/2005 | Sumegi | 514/318 |
| 9,126,056 | B2* | 9/2015 | Chen | A61K 8/4953 |
| 2005/0043328 | A1* | 2/2005 | Dolezal et al. | 514/263.37 |
| 2006/0247199 | A1* | 11/2006 | Newell | A61K 39/395 514/44 R |
| 2007/0161582 | A1* | 7/2007 | Mijikovic et al. | 514/43 |
| 2010/0190806 | A1* | 7/2010 | Spichal | A01N 43/90 514/263.4 |
| 2011/0263618 | A1* | 10/2011 | Chen et al. | 514/263.4 |
| 2014/0309242 | A1* | 10/2014 | Chen et al. | 514/263.4 |

FOREIGN PATENT DOCUMENTS

WO    WO 2009/032057    *    3/2009

OTHER PUBLICATIONS

Glossary of medical education terms, Institute of International Medical Education. http://www.iime.org/glossary.htm Accessed in Mar. 2013.*

(Continued)

*Primary Examiner* — Yih-Horng Shiao
(74) *Attorney, Agent, or Firm* — McCarter & English, LLP; Yu Lu; Joshua J. Galgano

(57) ABSTRACT

The present invention relates to a method for treating disease or condition susceptible to amelioration by AMPK activators and compounds of formula which are useful to activate AMP-activated protein kinase (AMPK) and the use of the compounds in the prevention or treatment of disease, including pre-diabetes, type 2 diabetes, syndrome X, metabolic syndrome and obesity.

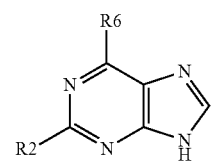

(I)

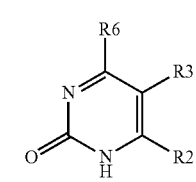

(II)

6 Claims, No Drawings

(56) References Cited

OTHER PUBLICATIONS

Dunkley AJ, Charles K, et al. Effectiveness of interventions for reducing diabetes and cardiovascular disease risk in people with metabolic syndrome: systematic review and mixed treatment comparison meta-analysis. Diabetes Obs Metab 14:616-625, Jul. 2012.*
Yanovski et al. Long-term Drug Treatment for Obesity a Systematic and Clinical Review. JAMA 311:74-86, 2014.*
Serrano M. Shifting senescence into quiescence by turning up p53. Cell Cycle 9:21, 4256-4257; Nov. 1, 2010.*
Montgomery et al. Synthesis of Potential Anticancer Agents. XI. N2,6-Alkyl Derivatives of 2,6-Diaminopurine. Journal of the American Chemical Society (1958), 80, 404-8.*
Vesely et al. Inhibition of cyclin-dependent kinases by purine analogues. Eur. J. Biochem. 224, 771-786 (1994).*

* cited by examiner

METHOD FOR TREATING DISEASE OR CONDITION SUSCEPTIBLE TO AMELIORATION BY AMPK ACTIVATORS AND COMPOUNDS OF FORMULA WHICH ARE USEFUL TO ACTIVATE AMP-ACTIVATED PROTEIN KINASE (AMPK)

BACKGROUND OF THE INVENTION

1. Technical Field

The present invention relates to a method for treating disease or condition susceptible to amelioration by AMPK activators and compounds of formula which are useful to activate AMP-activated protein kinase (AMPK) and the use of the compounds in the prevention or treatment of disease, including pre-diabetes, type 2 diabetes, syndrome X, metabolic syndrome and obesity.

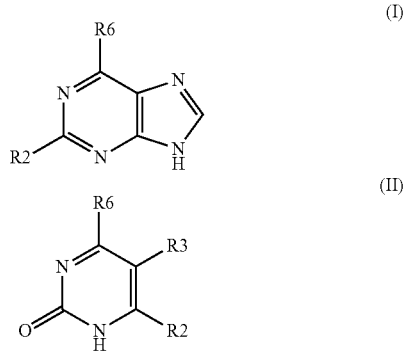

2. Description of Related Art

Adenosine 5'-monophosphate-activated protein kinase (AMPK) is a cellular energy sensor and a responder to energy demand. AMPK is a heterotrimer composed of catalytic α subunit and regulatory β, γ subunits. All these subunits are highly conserved in eukaryotes. The activation of AMPK is through phosphorylation on the conserved $172^{th}$-threonine residue of α subunit by upstream kinases-such as LKB1, $Ca^{2+}$/Calmodulin dependent kinase, and TAK1. High AMP/ATP ratio caused by physiological or pathological stress activates AMPK. Upon activation, AMPK activates catabolic pathway and inhibits anabolism which in term restores cellular energy balance by decreasing ATP consumption and promoting ATP generation.

As a regulator of energy homeostasis, AMPK has been suggested to be a potential drug target for metabolic syndromes including type II diabetes, cardio-vascular disease, and fatty liver disease. Many of the metabolic syndromes are linked to insulin resistance. Insulin resistance is a pathological condition in which cells fail to respond to insulin thus excess glucose in the blood stream cannot be removed into skeletal muscle or fat tissue. The activation of AMPK increases protein level of GLUT4, a glucose transporter, via transcriptional regulation and induces GLUT4 translocation to the plasma membrane in muscle cells in an insulin independent manner resulting in increases in the rate of cellular glucose uptake. Activation of AMPK also inhibits fatty acids and cholesterol synthesis via suppressing acetyl-CoA carboxylase and HMG-CoA reductase, respectively. In addition, activation of AMPK leads to inhibition of several transcription factors, including SREBP-1c, ChREBP and HNF-4a, and down-regulates the expression of enzymes which are mainly involved in fatty acid synthesis and gluconeogenesis. These findings support the idea that AMPK is a target of choice in the treatment of metabolic syndrome, in particular, diabetes.

AMP is the natural activator of AMPK in cells. However, it's an unstable compound and extracellular application of AMP might trigger purinergic receptor-mediated signaling (that might lead to apoptosis etc). As a result, many researchers have been devoted to AMPK activator development. Compounds such as 5-amino-1-β-D-ribofuranosyl-imidazole-4-carboxamide (AICAR) and metformin can activate AMPK at high concentration in vivo. Metformin has been used to treat pre-diabetes, insulin resistance, syndrome X and type 2 diabetes. However, its side effects include lactic acidosis, especially when patients have renal insufficiency. Developing novel AMPK activators with lower effective concentration and fewer side effects is therefore urgent.

BRIEF SUMMARY OF THE INVENTION

The present invention is direct to compounds of formulae I and II and the tautomer

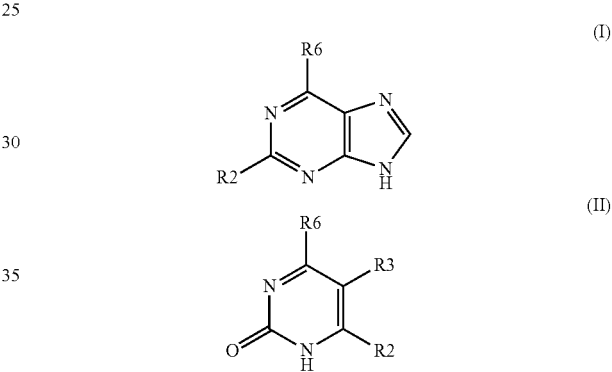

wherein R2 is hydrogen, halogen, hydroxy group, amino group or amino group with mono or di-substituted with hydrocarbon group at most 10 carbon, mercapto, carboxyl, nitro, sulfo, alkyl, alkylamino, alkylmercapto, alkoxy, cycloalkyl, substituted alkyl, substituted alkenyl, substituted alkynyl, acyl, aryl, substituted aryl, aryloxy;

R6 is hydroxy group, amino group, mercapto group, —NHR group, where R is halogen, hydroxy group, amino group or amino group with mono or di-substituted with hydrocarbon group at most 10 carbon, mercapto, carboxyl, nitro, sulfo, alkyl, alkylamino, alkylmercapto, alkoxy, cycloalkyl, substituted alkyl, substituted alkenyl, substituted alkynyl, acyl, aryl, substituted aryl, aryloxy;

R3 is hydrogen or alkyl group at most 10 carbon; or its tautomer or pharmaceutically acceptable salts thereof, and an AMPK activator which comprises said purine and pyrimidine derivatives or pharmaceutical acceptable salts thereof as an active compound.

The generic substitutes have meanings identical with definition, wherein

"hydroxy" refers to the group —OH;
"halogen" refers to F, Cl, Br, I;
"amino" refers to the group —$NH_2$;
"mercapto" refers to the group —SH;
"carboxyl" refers to the group —C(O)OR, where R is hydrogen, alkyl, substituted alkyl, acryl, substitute acryl s defined herein;

"nitro" refers to the group —NO₂;

"sulfo" refers to the group —SO₃R, whereas R is hydrogen, alkyl, or substituted alkyl as defined herein;

"alkyl" refers to linear or branched chain at most 10 carbons which is saturated or unsaturated being selected from the group such as methyl, propyl, isopropyl, butyl, allyl, vinyl, ethinyl, propargyl, hexen-2-yl and the like exemplifying this term;

"substituted alkyl" refers to alkyl including one to seven substituents such as hydroxy, mercapto, alkylamino, alkylmercapto, halogen, alkoxy, acyloxy, amino, carboxy, sulfo, acyl, and the like, whereby these group may be attach to any carbon of the alkyl moiety;

"alkylamino" refers to the group —NRR', where R and R' are independently hydrogen, alkyl, substituted alkyl, acryl, substituted acryl as defined herein;

"alkylmercapto" refers to the group —SR, where R is alkyl, substituted alkyl, acryl, substituted acryl as defined herein;

"alkoxy" refers to the group —OR, where R is alkyl, substituted alkyl, acryl, substituted acryl as defined herein;

"cycloalkyl' refers to a cyclic or polycyclic alky group containing 3 to 15 carbon.

"acyl" refers to the group —C(O)R, where R is hydrogen, alkyl, substituted alkyl, acryl, substituted acryl as defined herein;

"aryl" refers to an aromatic carbocyclic group;

"substituted aryl" refers to aryl group containing substituents such as halogen, hydroxy, amino, mercapto, alkoxy, sulfo, carboxy, alkyl as defined herein;

"aryloxy" refers to the group —OAr, where Ar is aryl, substitute aryl as defined herein;

Therefore, particularly preferred AMPK activating compounds include adenine, 2-amino-6-methylaminopurine, 2-amino-6-ethylaminopurine, 2-amino-6-isobutylaminopurine, 2-amino-6-propylaminopurine, 2-amino-6-isopentylaminopurine, 2-amino-6-hexylaminopurine, 2-amino-6-cyclopropylaminopurine, 2-amino-6-cyclobutylaminopurine, 2-amino-6-cyclopentylaminopurine, 2-amino-6-cyclohexylaminopurine, 2-amino-6-anilinopurine, 2-amino-6-(2-chloroanilino)purine, 2-amino-6-(3-chloroanilino)purine, 2-amino-6-(4-chloroanilino)purine, 2-amino-6-(2-bromoanilino)purine, 2-amino-6-(3-bromoanilino)purine, 2-amino-6-(4-bromoanilino)purine, 2-amino-6-(2-fluoroanilino)purine, 2-amino-6-(3-fluoroanilino)purine, 2-amino-6-(4-fluoroanilino)purine, 2-amino-6-benzylaminopurine, 2-amino-6-(2-methylbenzylamino)purine, 2-amino-6-(3-methylbenzylamino)purine, 2-amino-6-(4-methylbenzylamino)purine, 2-amino-6-(2-chlorobenzylamino)purine, 2-amino-6-(3-chlorobenzylamino)purine, 2-amino-6-(4-chlorobenzylamino)purine, 2-amino-6-(2-fluorobenzylamino)purine, 2-amino-6-(3-fluorobenzylamino)purine, 2-amino-6-(4-fluorobenzylamino)purine, 2-amino-6-(3-iodobenzylamino)purine, 2-amino-6-(4-hydroxybenzylamin)purine, 2-amino-6-(2,3-dihydroxybenzylamino)purine, 2-amino-6-(3,4-dihydroxybenzylamino)purine, 2-amino-6-(2,4-dihydroxybenzylamino)purine, 2-amino-6-(2-methoxylbenzylamino)purine, 2-amino-6-(2,3-dimethoxybenzylamino)purine, 2-amino-6-(3,5-dimethoxybenzylamino)purine, 2-amino-6-(2,4,5-trimethoxybenzylamino)purine, 2-amino-6-(3,4,5-trimethoxybenzylamino)purine, 6-methylaminopurine, 6-ethylaminopurine, 6-propylaminopurine, 6-Isobutylaminopurine, 6-Isopentylaminopurine, 6-hexylaminopurine, 6-cyclopropylaminopurine, 6-cyclobutylaminopurine, 6-cyclopantylaminopurine, 6-cyclohexylaminopurine, 6-anilinopurine, 6-(2-chloroanilino)purine, 6-(3-chloroanilino)purine, 6-(4-chloroanilino)purine, 6-(2-bromoanilino)purine, 6-(3-bromoanilino)purine, 6-(4-bromoanilino)purine, 6-(2-fluoroanilino)purine, 6-(3-fluoroanilino)purine, 6-(4-fluoroanilino)purine, 6-benzylaminopurine, 6-(2-methylbenzylamino)purine, 6-(3-methylbenzylamino)purine, 6-(4-methylbenzylamino)purine, 6-(2-chlorobenzylamino)purine, 6-(3-chlorobenzylamino)purine, 6-(4-chlorobenzylamino)purine, 6-(2-fluorobenzylamino)purine, 6-(3-fluorobenzylamino)purine, 6-(4-fluorobenzylamino)purine, 6-(3-iodobenzylamino)purine, 6-(4-hydroxybenzylamino)purine, 6-(2,3-dihydroxybenzylamino)purine, 6-(3,4-dihydroxybenzylamino)purine, 6-(2,4-dihydroxybenzylamino)purine, 6-(2-methoxylbenzylamino)purine, 6-(2,3-dimethoxybenzylamino)purine, 6-(3,5-dimethoxybenzylamino)purine, 6-(2,4,5-trimethoxybenzylamino)purine, 6-(3,4,5-trimethoxybenzylamino)purine, 2-hydroxy-6-methylaminopurine, 2-hydroxy-6-ethylaminopurine, 2-hydroxy-6-isobutylaminopurine, 2-hydroxy-6-propylaminopurine, 2-hydroxy-6-isopentylaminopurine, 2-hydroxy-6-hexylaminopurine, 2-hydroxy-6-cyclopropylaminopurine, 2-hydroxy-6-cyclobutylaminopurine, 2-hydroxy-6-cyclopentylaminopurine, 2-hydroxy-6-cyclohexylaminopurine, 2-hydroxy-6-anilinopurine, 2-hydroxy-6-(2-chloroanilino)purine, 2-hydroxy-6-(3-chloroanilino)purine, 2-hydroxy-6-(4-chloroanilino)purine, 2-hydroxy-6-(2-bromoanilino)purine, 2-hydroxy-6-(3-bromoanilino)purine, 2-hydroxy-6-(4-bromoanilino)purine, 2-hydroxy-6-(2-fluoroanilino)purine, 2-hydroxy-6-(3-fluoroanilino)purine, 2-hydroxy-6-(4-fluoroanilino)purine, 2-hydroxy-6-benzylaminopurine, 2-hydroxy-6-(2-methylbenzylamino)purine, 2-hydroxy-6-(3-methylbenzylamino)purine, 2-hydroxy-6-(4-methylbenzylamino)purine, 2-hydroxy-6-(2-chlorobenzylamino)purine, 2-hydroxy-6-(3-chlorobenzylamino)purine, 2-hydroxy-6-(4-chlorobenzylamino)purine, 2-hydroxy-6-(2-fluorobenzylamino)purine, 2-hydroxy-6-(3-fluorobenzylamino)purine, 2-hydroxy-6-(4-fluorobenzylamino)purine, 2-hydroxy-6-(3-iodobenzylamino)purine, 2-hydroxy-6-(4-hydroxybenzylamin)purine, 2-hydroxy-6-(2,3-dihydroxybenzylamino)purine, 2-hydroxy-6-(3,4-dihydroxybenzylamino)purine, 2-hydroxy-6-(2,4-dihydroxybenzylamino)purine, 2-hydroxy-6-(2-methoxylbenzylamino)purine, 2-hydroxy-6-(2,3-dimethoxybenzylamino)purine, 2-hydroxy-6-(3,5-dimethoxybenzylamino)purine, 2-hydroxy-6-(2,4,5-trimethoxybenzylamino)purine, 2-hydroxy-6-(3,4,5-trimethoxybenzylamino)purine, 2-methyl-6-methylaminopurine, 2-methyl-6-ethylaminopurine, 2-methyl-6-isobutylaminopurine, 2-methyl-6-propylaminopurine, 2-methyl-6-isopentylaminopurine, 2-methyl-6-hexylaminopurine, 2-methyl-6-cyclopropylaminopurine, 2-methyl-6-cyclobutylaminopurine, 2-methyl-6-cyclopentylaminopurine, 2-methyl-6-cyclohexylaminopurine, 2-methyl-6-anilinopurine, 2-methyl-6-(2-chloroanilino)purine, 2-methyl-6-(3-chloroanilino)purine, 2-methyl-6-(4-chloroanilino)purine, 2-methyl-6-(2-bromoanilino)purine, 2-methyl-6-(3-bromoanilino)purine, 2-methyl-6-(4-bromoanilino)purine, 2-methyl-6-(2-fluoroanilino)purine, 2-methyl-6-(3-fluoroanilino)purine, 2-methyl-6-(4-fluoroanilino)purine, 2-methyl-6-benzylaminopurine, 2-methyl-6-(2-methylbenzylamino)purine, 2-methyl-6-(3-methylbenzylamino)purine, 2-methyl-6-(4-methylbenzylamino)purine, 2-methyl-6-(2-chlorobenzylamino)purine, 2-methyl-6-(3-chlorobenzylamino)purine, 2-methyl-6-(4-chlorobenzylamino)purine, 2-methyl-6-(2-fluorobenzylamino)purine, 2-methyl-6-(3-fluorobenzylamino)purine, 2-methyl-6-(4-fluorobenzylamino)purine, 2-methyl-6-(3-iodobenzylamino)purine, 2-methyl-6-(4-hydroxybenzylamin)purine, 2-methyl-6-(2,3-dihydroxybenzylamino)purine, 2-methyl-6-(3,4-dihydroxybenzylamino)purine, 2-methyl-6-(2,4-dihydroxybenzylamino)purine, 2-methyl-6-(2-methoxylbenzylamino)purine, 2-methyl-6-(2,3-dimethoxybenzylamino) purine, 2-methyl-6-(3,5-dimethoxybenzylamino)purine, 2-methyl-6-(2,4,5-trimethoxybenzylamino)purine, 2-methyl-6-(3,4,5-trimethoxybenzylamino)purine, 2 methylamino-6-aminopurine, 2-ethylamino-6-aminopurine, 2-isobutylamino-6-aminopurine, 2-propylamino-6-aminopurine, 2-isopentylamino-6-aminopurine, 2-hexylamino-6-aminopurine, 2-cyclopropylamino-6-aminopurine, 2-cyclobutylamino-6-aminopurine, 2-cyclopentylamino-6-aminopurine, 2-cyclohexylamino-6-aminopurine, 2-anilino-6-aminopurine, 2-(2-chloroanilino)-6-aminopurine, 2-(3-chloroanilino)-6-aminopurine, 2-(4-chloroanilino)-6-aminopurine, 2-(2-bromoanilino)-6-aminopurine, 2-(3-bromoanilino)-6-aminopurine, 2-(4-bromoanilino)-6-aminopurine, 2-(2-fluoroanilino)-6-aminopurine, 2-(3-fluoroanilino)-6-aminopurine, 2-(4-fluoroanilino)-6-aminopurine, 2-benzylamino-6-aminopurine, 2-(2-methylbenzylamino)-6-aminopurine, 2-(3-methylbenzylamino)-6-aminopurine, 2-(4-methylbenzylamino)-6-aminopurine, 2-(2-chlorobenzylamino)-6-aminopurine, 2-(3-chlorobenzylamino)-6-aminopurine, 2-(4-chlorobenzylamino)-6-aminopurine, 2-(2-fluorobenzylamino)-6-aminopurine, 2-(3-fluorobenzylamino)-6-aminopurine, 2-(4-fluorobenzylamino)-6-aminopurine, 2-(3-iodobenzylamino)-6-aminopurine, 2-(4-hydroxybenzylamino)-6-aminopurine, 2-(2,3-dihydroxybenzylamino)-6-aminopurine, 2-(3,4-dihydroxybenzylamino)-6-aminopurine, 2-(2,4-dihydroxybenzylamino)-6-aminopurine, 2-(2-methoxylbenzylamino)-6-aminopurine, 2-(2,3-dimethoxybenzylamino)-6-aminopurine, 2-(3,5-dimethoxybenzylamino)-6-aminopurine, 2-(2,4,5-trimethoxybenzylamino)-6-aminopurine, 2-(3,4,5-trimethoxybenzylamino)-6-aminopurine, 2-methylamino-6-hydroxypurine, 2-ethylamino-6-hydroxypurine, 2-isobutylamino-6-hydroxypurine, 2-propylamino-6-hydroxypurine, 2-isopentylamino-6-hydroxypurine, 2-hexylamino-6-hydroxypurine, 2-cyclopropylamino-6-hydroxypurine, 2-cyclobutylamino-6-hydroxypurine, 2-cyclopentylamino-6-hydroxypurine, 2-cyclohexylamino-6-hydroxypurine, 2-anilino-6-hydroxypurine, 2-(2-chloroanilino)-6-hydroxypurine, 2-(3-chloroanilino)-6-hydroxypurine, 2-(4-chloroanilino)-6-hydroxypurine, 2-(2-bromoanilino)-6-hydroxypurine, 2-(3-bromoanilino)-6-hydroxypurine, 2-(4-bromoanilino)-6-hydroxypurine, 2-(2-fluoroanilino)-6-hydroxypurine, 2-(3-fluoroanilino)-6-hydroxypurine, 2-(4-fluoroanilino)-6-hydroxypurine, 2-benzylamino-6-hydroxypurine, 2-(2-methylbenzylamino)-6-hydroxypurine, 2-(3-methylbenzylamino)-6-hydroxypurine, 2-(4-methylbenzylamino)-6-hydroxypurine, 2-(2-chlorobenzylamino)-6-hydroxypurine, 2-(3-chlorobenzylamino)-6-hydroxypurine, 2-(4-chlorobenzylamino)-6-hydroxypurine, 2-(2-fluorobenzylamino)-6-hydroxypurine, 2-(3-fluorobenzylamino)-6-hydroxypurine, 2-(4-fluorobenzylamino)-6-hydroxypurine, 2-(3-iodobenzylamino)-6-hydroxypurine, 2-(4-hydroxybenzylamino)-6-hydroxypurine, 2-(2,3-dihydroxybenzylamino)-6-hydroxypurine, 2-(3,4-dihydroxybenzylamino)-6-hydroxypurine, 2-(2,4-dihydroxybenzylamino)-6-hydroxypurine, 2-(2-methoxylbenzylamino)-6-hydroxypurine, 2-(2,3-dimethoxybenzylamino)-6-hydroxypurine, 2-(3,5-dimethoxybenzylamino)-6-hydroxypurine, 2-(2,4,5-trimethoxybenzylamino)-6-hydroxypurine, 2-(3,4,5-trimethoxybenzylamino)-6-hydroxypurine, 6-hydroxypurine, 6-mercaptopurine, $N^6$-methyladenine, 2-aminoadenine, 2-hydroxyadenine, 2-methyladenine, 2-amino-6-hydroxypurine, 2,6-dihydroxypurine, 2-methyl-6-hydroxypurine, 2-amino-6-mercaptopurine, 2-hydroxy-6-mercaptopurine, 2-methyl-6-mercaptopurine, 2-mercaptoadenine, 2-mercapto-6-hydroxypurine, 2,6-dimercaptopurine, 2-mercapto-6-methylaminopurine, 2-mercapto-6-ethylaminopurine, 2-mercapto-6-propylpurine, 2-ethyladenine, 2-ethyl-6-hydroxypurine, 2-ethyl-6-mercaptopurine, 2-ethyl-6-methylaminopurine, 2-ethyl-6-ethylaminopurine, 2-ethyl-6-propylaminopurine, 2-propyladenine, 2-propyl-6-hydroxypurine, 2-propyl-6-mercaptopurine, 2-propyl-6-methylaminopurine, 2-propyl-6-ethylaminopurine, 2-propyl-6-propylaminopurine, 2-amino-6-benzylaminopurine, 2-ethyl-6-benzylaminopurine, 2-propyl-6-benzylaminopurine, 2-ethyl-6-anilinopurine, 2-propyl-6-anilinopurine, 2-benzyl-adenine, 2-benzyl-6-hydroxypurine, 2-benzyl-6-mercaptopurine, 2-benzyl-6-methylaminopurine, 2-benzyl-6-ethylaminopurine, 2-benzyl-6-propylaminopurine, 2-phenyl-adenine, 2-phenyl-6-hydroxypurine, 2-phenyl-6-mercaptopurine, 2-phenyl-6-methylaminopurine, 2-phenyl-6-ethylaminopurine, 2-phenyl-6-propylaminopurine, 2-mercapto-$N^6$-2-isopentenyladenine, 2-ethyl-$N^6$-2-isopentenyladenine, 2-propyl-$N^6$-2-isopentenyladenine, 2-benzyl-$N^6$-2-isopentenyladenine, 2-phenyl-$N^6$-2-isopentenyladenine, 2-chloroadenine, 2-chloro-6-hydroxypurine, 2-chloro-6-mercaptopurine, 2-chloro-6-methylaminopurine, 2-chloro-6-ethylpurine, 2-chloro-6-propylaminopurine, 2-chloro-6-benzylaminopurine, 2-chloro-6-anilinopurine, 2-chloro-$N^6$-2-isopentenyladenine, 2-fluoroadenine, 2-fluoro-6-hydroxypurine, 2-fluoro-6-mercaptopurine, 2-fluoro-6-methylaminopurine, 2-fluoro-6-ethylpurine, 2-fluoro-6-propylaminopurine, 2-fluoro-6-benzylaminopurine, 2-fluoro-6-anilinopurine, 2-fluro-$N^6$-2-isopentenyladenine, 2-bromoadenine, 2-bromo-6-hydroxypurine, 2-bromo-6-mercaptopurine, 2-bromo-6-methylaminopurine, 2-bromo-6-ethylpurine, 2-bromo-6-propylaminopurine, 2-bromo-6-benzylaminopurine, 2-bromo-6-anilinopurine, 2-bromo-$N^6$-2-isopentenyladenine, 2-iodoadenine, 2-iodo-6-hydroxypurine, 2-iodo-6-mercaptopurine, 2-iodo-6-methylaminopurine, 2-iodo-6-ethylpurine, 2-iodo-6-propylaminopurine, 2-iodo-6-benzylaminopurine, 2-iodo-6-anilinopurine, 2-iodo-$N^6$-2-isopentenyladenine, 2-mercapto-$N^6$-cyclohexyladenine, 2-propyl-$N^6$-cyclohexyladenine, 2-ethyl-$N^6$-cyclohexyladenine, 2-benzyl-$N^6$-cyclohexyladenine, 2-phenyl-$N^6$-cyclohexyladenine, 2-chloro-$N^6$-cyclohexyladenine, 2-fluoro-$N^6$-cyclohexyladenine, 2-bromo-$N^6$-cyclohexyladenine, 2-iodo-$N^6$-cyclohexyladenine, 2-amino-6-(4-Hydroxy-3-methylbut-2-enylamino)purine, 2-hydroxy-6-(4-Hydroxy-3-methylbut-2-enylamino)purine, 2-mercapto-6-(4-Hydroxy-3-methylbut-2-enylamino)purine, 2-methyl-6-(4-Hydroxy-3-methylbut-2-enylamino)purine, 2-ethyl-6-(4-Hydroxy-3-methylbut-2-enylamino)purine, 2-propyl-6-(4-Hydroxy-3-methylbut-2-enylamino)purine, 2-benzyl-6-(4-Hydroxy-3-methylbut-2-enylamino)purine, 2-phenyl-6-(4-Hydroxy-3-methylbut-2-enylamino)purine, 2-chloro-6-(4-Hydroxy-3-methylbut-2-enylamino)purine, 2-fluoro-6-(4-Hydroxy-3-methylbut-2-enylamino)purine, 2-bromo-6-(4-Hydroxy-3-methylbut-2-enylamino)purine, 2-iodo-6-(4-Hydroxy-3-methylbut-2-enylamino)purine, 2-cyclohexyl-6-(4-Hydroxy-3-methylbut-2-enylamino)purine, 2-amino-6-Furfurylaminopurine, 2-hydroxy-6-Furfurylaminopurine, 2-mercapto-6-Furfurylaminopurine, 2-methyl-6-Furfurylaminopurine, 2-ethyl-6-Furfurylaminopurine, 2-propyl-6-Furfurylaminopurine, 2-benzyl-6-Furfurylaminopurine, 2-phenyl-6-Furfurylaminopurine, 2-chloro-6-Furfurylaminopurine, 2-fluoro-6-Furfurylaminopurine, 2-bromo-6-Furfurylaminopurine, 2-iodo-6-Furfurylaminopurine, 2-cyclohexyl-6-Furfurylaminopurine, 2-amino-6-acetylaminopurine, 2-hydroxy-6-acetylaminopurine, 2-mercapto-6-acetylaminopurine, 2-methyl-6-acetylaminopurine, 2-ethyl-6-acetylaminopurine, 2-propyl-6-acetylaminopurine, 2-benzyl-6-acetylaminopurine, 2-phenyl-6-acetylaminopurine, 2-chloro-6-acetylaminopurine, 2-fluoro-6-acetylaminopurine, 2-bromo-6-acetylaminopurine, 2-iodo-6-acetylaminopurine, 2-cyclohexyl-6-acetylaminopurine, 2-dimethylamino-6-hydroxypurine, guanine, xanthine, hypoxanthine, 6-thioguanine, 5-methylcytosine, 5,6-dihydrouracil, thymine, cytosine, uracil, 5-fluorouracil, floxuridine, 6-azauracil, each of which may be present as a salt, a hydrate, in form as a prodrug or as a metabolite.

According to one embodiment of the present invention there is provided a method of treating disease regulated by activation of AMPK which are useful for the prevention or treatment of pre-diabetes administrating a therapeutically effective amount of a compound of formula (I) in a mammal.

According to one embodiment of the present invention there is provided a method of treating disease regulated by activation of AMPK which are useful for the prevention or treatment of pre-diabetes administrating a therapeutically effective amount of a compound of formula (II) in a mammal.

According to one embodiment of the present invention there is provided a method of treating disease regulated by activation of AMPK which are useful for the prevention or treatment of insulin resistance administrating a therapeutically effective amount of a compound of formula (I) in a mammal.

According to one embodiment of the present invention there is provided a method of treating disease regulated by activation of AMPK which are useful for the prevention or treatment of insulin resistance administrating a therapeutically effective amount of a compound of formula (II) in a mammal.

According to one embodiment of the present invention there is provided a method of treating disease regulated by activation of AMPK which are useful for the prevention or treatment of type 2 diabetes administrating a therapeutically effective amount of a compound of formula (I) in a mammal.

According to one embodiment of the present invention there is provided a method of treating disease regulated by activation of AMPK which are useful for the prevention or treatment of type 2 diabetes administrating a therapeutically effective amount of a compound of formula (II) in a mammal.

According to one embodiment of the present invention there is provided a method of treating disease regulated by activation of AMPK which are useful for the prevention or treatment of syndrome X administrating a therapeutically effective amount of a compound of formula (I) in a mammal.

According to one embodiment of the present invention there is provided a method of treating disease regulated by activation of AMPK which are useful for the prevention or treatment of syndrome X administrating a therapeutically effective amount of a compound of formula (II) in a mammal.

According to one embodiment of the present invention there is provided a method of treating disease regulated by activation of AMPK which are useful for the prevention or treatment of metabolic syndrome administrating a therapeutically effective amount of a compound of formula (I) in a mammal.

According to one embodiment of the present invention there is provided a method of treating disease regulated by activation of AMPK which are useful for the prevention or treatment of metabolic syndrome administrating a therapeutically effective amount of a compound of formula (II) in a mammal.

According to one embodiment of the present invention there is provided a method of treating disease regulated by activation of AMPK which are useful for the prevention or treatment of obesity administrating a therapeutically effective amount of a compound of formula (I) in a mammal.

According to one embodiment of the present invention there is provided a method of treating disease regulated by activation of AMPK which are useful for the prevention or treatment of obesity administrating a therapeutically effective amount of a compound of formula (II) in a mammal.

According to one embodiment of the present invention there is provided a pharmaceutical composition comprising a therapeutically effect amount of a compound of formula (I) in combination with pharmaceutically suitable carrier.

According to one embodiment of the present invention there is provided a pharmaceutical composition comprising a therapeutically effect amount of a compound of formula (II) in combination with pharmaceutically suitable carrier.

According to one embodiment of the present invention, the pharmaceuticals composition may additionally including second pharmaceutical agent for treatment of pre-diabetes, insulin resistance, type 2 diabetes, syndrome X, metabolic syndrome. The suitable second pharmaceutical agents include various biguanides, thiazolidinediones, thienopyridones, and other AMPK activators.

As set forth herein, the present invention includes administering pharmaceutically effect amount of any compounds of formula (I) and (II) and the salts and prodrugs thereof to a mammal. Preferably, the present invention also includes administering pharmaceutically effect amount of any compounds of formula (I) and (II) to a human and more preferable to a human in need of treatment for any disorders set forth herein.

BRIEF DESCRIPTION OF THE DRAWINGS

NO DRAWING

DETAILED DESCRIPTION OF THE INVENTION

Definition

"AMPK" used herein refers to adenosine 5'-monophosphate-activated protein kinase.

"pre-diabetes" used herein refers to a physiological condition characterized by a fasting blood sugar higher than 100 mg/dL but below than 140 mg/dL.

"insulin resistance" used herein refers to a physiological condition in which whole body or tissues including liver, skeletal muscle, adipose tissue fail to response to insulin.

"type 2 diabetes" used herein also known as noninsulin-dependent diabetes mellitus (NIDDM) or adult-onset diabetes. It refers to a metabolic disorder caused by insufficient insulin production or insulin resistance which often manifested by a fasting glucose higher than 140 mg/dL.

"syndrome X" used herein refers to a condition characterized by symptoms of at least two of the following: Fasting hyperglycemia (non-insulin dependent diabetes), high blood pressure, high triglycerides, low HDL cholesterol.

Example 1

2-amino-6-(3-chlorobenzylamino)purine 4 mmol of 2-amino-6-chloropurine were dissolved in 20 mL of butanol and then 5 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>98%. Yield 95%.

Table 1 compound prepared by the method of example 1

| | Compounds prepared by the method of example 1 | | | |
|---|---|---|---|---|
| | CHN analysis Found/Calculated | | | ESI-MS |
| $R^6$ substitution | % C | % H | % N | [M + H$^+$] |
| methylamino | 43.5/43.9 | 5.1/4.9 | 51.4/51.2 | 165 |
| ethylamino | 47.0/47.2 | 5.5/5.7 | 47.5/47.2 | 179 |
| isobutylamino | 52.5/52.4 | 6.2/6.8 | 41.3/40.7 | 207 |
| propylamino | 50.3/50.0 | 6.2/6.3 | 43.5/43.7 | 193 |
| isopentylamino | 54.4/54.5 | 7.3/7.3 | 38.3/38.2 | 221 |
| hexylamino | 56.0/56.4 | 7.6/7.7 | 36.4/35.9 | 235 |
| cyclopropylamino | 49.9/50.5 | 5.5/5.3 | 44.6/44.2 | 191 |
| cyclobutylamino | 53.0/52.9 | 6.1/5.9 | 40.9/41.1 | 205 |
| cyclopentylamino | 54.5/55.0 | 6.3/6.5 | 39.2/38.5 | 219 |
| cyclohexylamino | 56.8/56.9 | 6.8/6.9 | 36.4/36.2 | 233 |
| anilino | 58.5/58.4 | 4.6/4.5 | 36.9/37.1 | 227 |
| 2-chloroanilino | 51.0/50.7 | 3.4/3.5 | 32.3/32.2 | 261 |
| 3-chloroanilino | 50.2/50.7 | 3.7/3.5 | 32.8/32.2 | 261 |
| 4-chloroanilino | 50.6/50.7 | 3.7/3.5 | 32.5/32.2 | 261 |
| 2-bromoanilino | 42.5/43.3 | 3.3/3.0 | 27.1/27.5 | 306 |
| 3-bromoanilino | 42.2/43.3 | 3.5/3.0 | 27.6/27.5 | 306 |
| 4-bromoanilino | 43.1/43.3 | 2.9/3.0 | 27.7/27.5 | 306 |
| 2-fluoroanilino | 54.0/54.1 | 3.5/3.7 | 34.6/34.4 | 245 |
| 3-fluoroanilino | 54.4/54.1 | 3.8/3.7 | 34.1/34.4 | 245 |
| 4-fluoroanilino | 54.7/54.1 | 3.6/3.7 | 34.5/34.4 | 245 |
| benzylamino | 59.6/60.0 | 5.2/5.0 | 35.2/35.0 | 241 |
| 2-methylbenzylamino | 61.1/61.4 | 5.4/5.5 | 33.5/33.0 | 255 |
| 3-methylbenzylamino | 61.5/61.4 | 5.3/5.5 | 33.2/33.0 | 255 |
| 4-methylbenzylamino | 61.8/61.4 | 5.7/5.5 | 32.5/33.0 | 255 |
| 2-chlorobenzylamino | 51.1/52.5 | 4.3/4.0 | 31.1/30.6 | 276 |
| 3-chlorobenzylamino | 52.1/52.5 | 3.9/4.0 | 31.5/30.6 | 276 |
| 4-chlorobenzylamino | 52.6/52.5 | 3.8/4.0 | 30.4/30.6 | 276 |
| 2-fluorobenzylamino | 55.2/55.8 | 4.2/4.3 | 32.9/32.5 | 259 |
| 3-fluorobenzylamino | 56.1/55.8 | 4.0/4.3 | 32.6/32.5 | 259 |
| 4-fluorobenzylamino | 55.3/55.8 | 4.5/4.3 | 32.6/32.5 | 259 |
| 3-iodobenzylamino | 40.1/39.4 | 2.7/3.0 | 23.5/23.0 | 367 |
| 4-hydroxybenzylamino | 56.1/56.2 | 4.8/4.7 | 33.0/32.8 | 257 |
| 2,3-dihydroxybenzylamino | 53.1/52.9 | 4.0/4.4 | 30.5/30.9 | 273 |
| 3,4-dihydroxybenzylamino | 53.2/52.9 | 4.5/4.4 | 30.1/30.9 | 273 |
| 2,4-dihydroxybenzylamino | 53.6/52.9 | 4.3/4.4 | 30.8/30.9 | 273 |
| 2-methoxylbenzylamino | 57.1/57.8 | 5.5/5.2 | 31.3/31.1 | 271 |
| 2,3-dimethoxybenzylamino | 56.4/56.0 | 5.8/5.4 | 27.1/28.0 | 301 |
| 3,5-dimethoxybenzylamino | 56.7/56.0 | 5.1/5.4 | 27.8/28.0 | 301 |
| 2,4,5-trimethoxybenzylamino | 54.1/54.5 | 5.0/5.5 | 25.6/25.4 | 331 |
| 3,4,5-trimethoxybenzylamino | 54.1/54.5 | 5.6/5.5 | 25.8/25.4 | 331 |

Example 2

6-(3-chlorobenzylamino)purine 4 mmol of 6-chloropurine were dissolved in 20 mL of butanol and then 5 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>97%. Yield 94%.

Table 2 compound prepared by the method of example 2

| | Compounds prepared by the method of example 2 | | | |
|---|---|---|---|---|
| | CHN analysis Found/Calculated | | | ESI-MS |
| $R^6$ substitution | % C | % H | % N | [M + H$^+$] |
| methylamino | 48.1/48.3 | 4.9/4.7 | 47.0/47.0 | 150 |
| ethylamino | 51.8/51.5 | 5.7/5.6 | 42.5/42.9 | 164 |
| propylamino | 54.0/54.2 | 6.4/6.3 | 39.6/39.5 | 178 |
| Isobutylamino | 56.7/56.5 | 7.1/6.9 | 36.2/36.6 | 192 |
| Isopentylamino | 58.8/58.5 | 7.5/7.4 | 37.7/34.1 | 206 |
| hexylamino | 60.1/60.2 | 7.9/7.8 | 32.0/31.9 | 220 |
| cyclopropylamino | 54.4/54.8 | 5.5/5.2 | 40.1/40.0 | 176 |
| cyclobutylamino | 56.2/57.1 | 6.2/5.9 | 37.6/37.0 | 190 |
| cyclopantylamino | 59.2/59.1 | 6.6/6.4 | 34.2/34.5 | 204 |
| cyclohexylamino | 60.5/60.8 | 7.1/7.0 | 32.4/32.2 | 218 |
| anilino | 62.6/62.5 | 4.5/4.3 | 32.9/33.2 | 212 |
| 2-chloroanilino | 53.5/53.8 | 3.4/3.3 | 28.8/28.5 | 247 |
| 3-chloroanilino | 53.2/53.8 | 3.4/3.3 | 28.7/28.5 | 247 |
| 4-chloroanilino | 53.6/53.8 | 3.1/3.3 | 28.9/28.5 | 247 |
| 2-bromoanilino | 44.9/45.5 | 3.1/2.8 | 24.4/24.1 | 291 |
| 3-bromoanilino | 45.9/45.5 | 3.1/2.8 | 25.0/24.1 | 291 |
| 4-bromoanilino | 44.9/45.5 | 3.4/2.8 | 24.2/24.1 | 291 |
| 2-fluoroanilino | 57.5/57.6 | 3.3/3.5 | 30.9/30.6 | 230 |
| 3-fluoroanilino | 57.9/57.6 | 3.4/3.5 | 30.5/30.6 | 230 |
| 4-fluoroanilino | 57.5/57.6 | 3.7/3.5 | 30.3/30.6 | 230 |
| benzylamino | 64.2/64.0 | 5.1/4.9 | 30.7/31.1 | 226 |
| 2-methylbenzylamino | 65.0/65.3 | 5.6/5.5 | 29.4/29.3 | 240 |
| 3-methylbenzylamino | 65.1/65.3 | 5.8/5.5 | 29.1/29.3 | 240 |
| 4-methylbenzylamino | 65.8/65.3 | 5.1/5.5 | 29.1/29.3 | 240 |
| 2-chlorobenzylamino | 55.2/55.5 | 3.8/3.9 | 27.1/27.0 | 261 |
| 3-chlorobenzylamino | 55.9/55.5 | 3.7/3.9 | 27.4/27.0 | 261 |
| 4-chlorobenzylamino | 55.6/55.5 | 3.6/3.9 | 27.8/27.0 | 261 |
| 2-fluorobenzylamino | 58.9/59.3 | 4.5/4.1 | 29.1/28.8 | 244 |
| 3-fluorobenzylamino | 59.1/59.3 | 4.2/4.1 | 28.7/28.8 | 244 |
| 4-fluorobenzylamino | 59.8/59.3 | 3.9/4.1 | 28.5/28.8 | 244 |
| 3-iodobenzylamino | 41.1/41.0 | 3.2/2.9 | 20.1/19.9 | 352 |
| 4-hydroxybenzylamino | 58.9/59.7 | 4.8/4.6 | 29.3/29.0 | 242 |
| 2,3-dihydroxybenzylamino | 56.9/56.0 | 4.1/4.3 | 26.4/27.2 | 258 |
| 3,4-dihydroxybenzylamino | 56.5/56.0 | 4.4/4.3 | 27.5/27.2 | 258 |
| 2,4-dihydroxybenzylamino | 56.7/56.0 | 4.1/4.3 | 26.9/27.2 | 258 |
| 2-methoxylbenzylamino | 60.6/61.2 | 4.5/5.1 | 28.1/27.4 | 256 |
| 2,3-dimethoxybenzylamino | 59.3/58.9 | 5.2/5.3 | 24.2/24.5 | 286 |
| 3,5-dimethoxybenzylamino | 59.2/58.9 | 5.6/5.3 | 24.1/24.5 | 286 |
| 2,4,5-trimethoxybenzylamino | 57.5/57.1 | 5.9/5.4 | 21.5/22.2 | 316 |
| 3,4,5-trimethoxybenzylamino | 57.4/57.1 | 5.5/5.4 | 21.6/22.2 | 316 |

Example 3

2-hydroxy-6-chloropurine 4 mmol of 2-amino-6-chloropurine were dissolved in 35 mL of 50% $H_2SO_4$ and then 5 mmol of sodium nitrate was added. The mixture was reacted at −10° C. for 2 hr and then 50° C. for another 1 hr. After cooling, the product was filter out and washed with water and butanol and crystallized from dimethyformamide or ethanol. HPLC: purity>98%. Yield 86%. MS (ESI) m/e 170.88 (M+H$^+$); $^1$H NMR (DMSO-d$_6$): 8.01 (s, 1H, =CH—N), 13.26 (s, 2H, OH and NH).

Example 4

2-hydroxy-6-(3-chlorobenzylamino)purine 3 mmol of 2-hydroxy-6-chloropurine from example 3 were dissolved in 20 mL of butanol and then 4 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>97%. Yield 93%.

Table 3 compound prepared by the method of example 4

Compounds prepared by the method of example 4

| $R^6$ substitution | CHN analysis Found/Calculated | | | ESI-MS [M + H$^+$] |
|---|---|---|---|---|
| | % C | % H | % N | |
| methylamino | 43.8/43.6 | 4.5/4.3 | 42.0/42.4 | 166 |
| ethylamino | 47.2/46.9 | 5.2/5.1 | 38.7/39.1 | 180 |
| propylamino | 49.8/49.7 | 5.3/5.7 | 36.5/36.2 | 194 |
| Isobutylamino | 52.4/52.2 | 6.5/6.3 | 33.5/33.8 | 208 |
| Isopentylamino | 54.1/54.3 | 6.9/6.8 | 31.9/31.7 | 222 |
| hexylamino | 56.7/56.2 | 7.1/7.3 | 29.9/29.8 | 236 |
| cyclopropylamino | 50.1/50.3 | 4.9/4.7 | 36.7/36.6 | 192 |
| cyclobutylamino | 52.9/52.7 | 5.5/5.4 | 39.6/34.1 | 206 |
| cyclopantylamino | 54.9/54.8 | 6.2/6.0 | 31.5/31.9 | 220 |
| cyclohexylamino | 57.8/56.6 | 6.1/6.5 | 29.5/30.0 | 234 |
| anilino | 57.9/58.1 | 4.1/4.0 | 30.9/30.8 | 228 |
| 2-chloroanilino | 50.1/50.5 | 3.3/3.1 | 27.1/26.8 | 263 |
| 3-chloroanilino | 50.3/50.5 | 3.6/3.1 | 26.6/26.8 | 263 |
| 4-chloroanilino | 49.8/50.5 | 3.5/3.1 | 27.3/26.8 | 263 |
| 2-bromoanilino | 43.5/43.2 | 2.9/2.6 | 22.1/22.9 | 307 |
| 3-bromoanilino | 43.1/43.2 | 2.1/2.6 | 23.6/22.9 | 307 |
| 4-bromoanilino | 43.5/43.2 | 2.4/2.6 | 23.1/22.9 | 307 |
| 2-fluoroanilino | 54.1/53.9 | 3.7/3.3 | 28.1/28.6 | 246 |
| 3-fluoroanilino | 54.6/53.9 | 3.5/3.3 | 27.9/28.6 | 246 |
| 4-fluoroanilino | 53.3/53.9 | 3.1/3.3 | 29.4/28.6 | 246 |
| benzylamino | 60.3/59.7 | 4.4/4.6 | 28.7/29.0 | 242 |
| 2-methylbenzylamino | 61.4/61.2 | 5.8/5.1 | 27.1/27.4 | 256 |
| 3-methylbenzylamino | 60.8/61.2 | 5.2/5.1 | 27.7/27.4 | 256 |
| 4-methylbenzylamino | 62.0/61.2 | 4.8/5.1 | 27.2/27.4 | 256 |
| 2-chlorobenzylamino | 52.5/52.3 | 3.5/3.7 | 25.8/25.4 | 277 |
| 3-chlorobenzylamino | 52.4/52.3 | 3.4/3.7 | 25.9/25.4 | 277 |
| 4-chlorobenzylamino | 52.1/52.3 | 3.9/3.7 | 25.5/25.4 | 277 |
| 2-fluorobenzylamino | 55.7/55.6 | 4.1/3.9 | 26.9/27.0 | 260 |
| 3-fluorobenzylamino | 55.2/55.6 | 4.2/3.9 | 27.3/27.0 | 260 |
| 4-fluorobenzylamino | 55.9/55.6 | 3.4/3.9 | 27.7/27.0 | 260 |
| 3-iodobenzylamino | 39.5/39.3 | 2.8/2.7 | 18.6/19.1 | 368 |
| 4-hydroxybenzylamino | 55.4/56.0 | 4.5/4.3 | 27.7/27.2 | 258 |
| 2,3-dihydroxybenzylamino | 52.9/52.7 | 3.8/4.1 | 25.4/25.6 | 274 |
| 3,4-dihydroxybenzylamino | 52.1/52.7 | 4.4/4.1 | 25.7/25.6 | 274 |
| 2,4-dihydroxybenzylamino | 52.9/52.7 | 4.6/4.1 | 24.8/25.6 | 274 |
| 2-methoxylbenzylamino | 57.1/57.6 | 4.2/4.8 | 26.7/25.8 | 272 |
| 2,3-dimethoxybenzylamino | 54.9/55.8 | 5.5/5.0 | 23.4/23.2 | 302 |
| 3,5-dimethoxybenzylamino | 56.1/55.8 | 4.8/5.0 | 23.4/23.2 | 302 |
| 2,4,5-trimethoxybenzylamino | 54.0/54.4 | 5.6/5.2 | 21.5/21.1 | 332 |
| 3,4,5-trimethoxybenzylamino | 54.5/54.4 | 5.3/5.2 | 21.3/21.1 | 332 |

Example 5

2-methyl-6-chloropurine 3 mmol of 2-Iodo-6-chloropurine was dissolved in 20 mL of butanol and then 4 mmol of MeMgCl was added. The mixture was reacted at 80° C. for 24 hr under Pd-catalysis. After cooling, the product was filter out and washed with water and butanol and crystallized from dimethyformamide or ethanol. HPLC: purity>97%. Yield 91%.

Example 6

2-methy-6-(3-chlorobenzylamino)purine 3 mmol of 2-methyl-6-chloropurine from example 5 were dissolved in 20 mL of butanol and then 4 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>98%. Yield 93%.

Table 4 compound prepared by the method of example 6

Compounds prepared by the method of example 6

| $R^6$ substitution | CHN analysis Found/Calculated | | | ESI-MS [M + H$^+$] |
|---|---|---|---|---|
| | % C | % H | % N | |
| methylamino | 51.4/51.5 | 5.9/5.6 | 42.7/42.9 | 164 |
| ethylamino | 54.5/54.2 | 6.4/6.3 | 39.1/39.5 | 178 |
| propylamino | 56.1/56.5 | 6.7/6.9 | 37.2/36.6 | 192 |
| Isobutylamino | 58.9/58.5 | 7.5/7.4 | 33.6/34.1 | 206 |
| Isopentylamino | 60.3/60.2 | 7.4/7.8 | 32.3/31.9 | 220 |
| hexylamino | 62.2/61.8 | 8.1/8.2 | 29.7/30.0 | 234 |
| cyclopropylamino | 57.5/57.1 | 6.3/5.9 | 36.2/37.0 | 190 |
| cyclobutylamino | 58.9/59.1 | 6.2/6.4 | 34.9/34.5 | 204 |
| cyclopantylamino | 60.7/60.8 | 7.3/7.0 | 32.0/32.2 | 218 |
| cyclohexylamino | 62.1/62.3 | 7.7/7.4 | 30.2/30.3 | 232 |
| anilino | 64.4/64.0 | 4.8/4.9 | 30.8/31.1 | 226 |
| 2-chloroanilino | 55.4/55.5 | 3.6/3.9 | 27.5/27.0 | 261 |
| 3-chloroanilino | 55.2/55.5 | 3.8/3.9 | 27.4/27.0 | 261 |
| 4-chloroanilino | 55.1/55.5 | 4.1/3.9 | 27.3/27.0 | 261 |
| 2-bromoanilino | 47.7/47.4 | 3.1/3.3 | 23.1/23.0 | 305 |
| 3-bromoanilino | 48.1/47.4 | 3.0/3.3 | 22.7/23.0 | 305 |
| 4-bromoanilino | 47.2/47.4 | 3.2/3.3 | 23.5/23.0 | 305 |
| 2-fluoroanilino | 59.5/59.3 | 4.4/4.1 | 28.2/28.8 | 244 |
| 3-fluoroanilino | 59.8/59.3 | 4.0/4.1 | 28.4/28.8 | 244 |
| 4-fluoroanilino | 59.1/59.3 | 3.7/4.1 | 29.4/28.8 | 244 |
| benzylamino | 65.5/65.3 | 5.7/5.5 | 28.8/29.3 | 240 |
| 2-methylbenzylamino | 66.8/66.4 | 5.9/6.0 | 27.3/27.6 | 254 |
| 3-methylbenzylamino | 66.9/66.4 | 5.4/6.0 | 27.7/27.6 | 254 |
| 4-methylbenzylamino | 65.9/66.4 | 6.2/6.0 | 27.9/27.6 | 254 |
| 2-chlorobenzylamino | 57.8/57.0 | 4.3/4.4 | 25.4/25.6 | 275 |
| 3-chlorobenzylamino | 57.2/57.0 | 4.8/4.4 | 25.1/25.6 | 275 |
| 4-chlorobenzylamino | 56.4/57.0 | 3.7/4.4 | 26.7/25.6 | 275 |
| 2-fluorobenzylamino | 61.1/60.7 | 4.9/4.7 | 27.0/27.2 | 258 |
| 3-fluorobenzylamino | 60.8/60.7 | 4.1/4.7 | 27.3/27.2 | 258 |
| 4-fluorobenzylamino | 60.9/60.7 | 4.8/4.7 | 27.4/27.2 | 258 |
| 3-iodobenzylamino | 43.3/42.8 | 3.3/3.3 | 18.9/19.2 | 366 |
| 4-hydroxybenzylamino | 61.1/61.2 | 4.1/5.1 | 28.2/27.4 | 256 |
| 2,3-dihydroxybenzylamino | 57.8/57.6 | 4.4/4.8 | 26.1/25.8 | 272 |
| 3,4-dihydroxybenzylamino | 57.3/57.6 | 5.2/4.8 | 25.6/25.8 | 272 |
| 2,4-dihydroxybenzylamino | 57.9/57.6 | 4.6/4.8 | 25.9/25.8 | 272 |
| 2-methoxylbenzylamino | 63.0/62.4 | 5.1/5.6 | 26.2/26.0 | 270 |
| 2,3-dimethoxybenzylamino | 59.7/60.2 | 5.5/5.7 | 23.8/23.4 | 300 |
| 3,5-dimethoxybenzylamino | 60.3/60.2 | 5.9/5.7 | 23.5/23.4 | 300 |
| 2,4,5-trimethoxybenzylamino | 58.8/58.3 | 5.4/5.8 | 21.5/21.3 | 330 |
| 3,4,5-trimethoxybenzylamino | 58.4/58.3 | 5.5/5.8 | 21.5/21.3 | 330 |

Example 7

2-(3-chlorobenzylamino)-6-aminopurine 4 mmol of 2-chloro-6-aminopurine were dissolved in 20 mL of butanol and then 5 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>95%. Yield 92%.

Table 5 compound prepared by the method of example 7

| Compounds prepared by the method of example 7 | | | | |
|---|---|---|---|---|
| | CHN analysis Found/Calculated | | | ESI-MS [M + H⁺] |
| R² substitution | % C | % H | % N | |
| methylamino | 44.4/43.9 | 4.8/4.9 | 50.8/51.2 | 165 |
| ethylamino | 47.1/47.2 | 5.9/5.7 | 47.0/47.2 | 179 |
| isobutylamino | 52.8/52.4 | 6.9/6.8 | 40.3/40.7 | 207 |
| propylamino | 49.4/50.0 | 6.6/6.3 | 44.0/43.7 | 193 |
| isopentylamino | 55.1/54.5 | 7.1/7.3 | 37.8/38.2 | 221 |
| hexylamino | 55.2/56.4 | 7.9/7.7 | 36.9/35.9 | 235 |
| Cyclopropylamino | 50.6/50.5 | 5.4/5.3 | 44.0/44.2 | 191 |
| Cyclobutylamino | 52.7/52.9 | 6.2/5.9 | 41.1/41.1 | 205 |
| cyclopentylamino | 55.4/55.0 | 6.5/6.5 | 38.1/38.5 | 219 |
| cyclohexylamino | 57.1/56.9 | 7.0/6.9 | 35.9/36.2 | 233 |
| anilino | 57.9/58.4 | 4.8/4.5 | 37.3/37.1 | 227 |
| 2-chloroanilino | 50.8/50.7 | 3.4/3.5 | 32.4/32.2 | 261 |
| 3-chloroanilino | 50.9/50.7 | 3.6/3.5 | 32.0/32.2 | 261 |
| 4-chloroanilino | 51.4/50.7 | 3.3/3.5 | 31.8/32.2 | 261 |
| 2-bromoanilino | 44.0/43.3 | 3.1/3.0 | 26.8/27.5 | 306 |
| 3-bromoanilino | 43.1/43.3 | 3.2/3.0 | 27.6/27.5 | 306 |
| 4-bromoanilino | 43.6/43.3 | 2.9/3.0 | 27.2/27.5 | 306 |
| 2-fluoroanilino | 54.2/54.1 | 3.8/3.7 | 34.5/34.4 | 245 |
| 3-fluoroanilino | 54.3/54.1 | 3.6/3.7 | 34.1/34.4 | 245 |
| 4-fluoroanilino | 54.5/54.1 | 3.6/3.7 | 34.1/34.4 | 245 |
| benzylamino | 59.1/60.0 | 5.4/5.0 | 35.5/35.0 | 241 |
| 2-methylbenzylamino | 60.9/61.4 | 5.7/5.5 | 33.4/33.0 | 255 |
| 3-methylbenzylamino | 61.5/61.4 | 5.2/5.5 | 33.3/33.0 | 255 |
| 4-methylbenzylamino | 61.8/61.4 | 5.6/5.5 | 32.6/33.0 | 255 |
| 2-chlorobenzylamino | 51.9/52.5 | 4.2/4.0 | 30.7/30.6 | 276 |
| 3-chlorobenzylamino | 52.8/52.5 | 3.9/4.0 | 30.5/30.6 | 276 |
| 4-chlorobenzylamino | 52.9/52.5 | 3.9/4.0 | 30.3/30.6 | 276 |
| 2-fluorobenzylamino | 55.9/55.8 | 4.5/4.3 | 32.7/32.5 | 259 |
| 3-fluorobenzylamino | 55.2/55.8 | 4.5/4.3 | 32.8/32.5 | 259 |
| 4-fluorobenzylamino | 56.1/55.8 | 4.2/4.3 | 32.1/32.5 | 259 |
| 3-iodobenzylamino | 39.0/39.4 | 3.0/3.0 | 23.1/23.0 | 367 |
| 4-hydroxybenzylamino | 56.8/56.2 | 4.5/4.7 | 32.5/32.8 | 257 |
| 2,3-dihydroxybenzylamino | 52.7/52.9 | 4.5/4.4 | 31.1/30.9 | 273 |
| 3,4-dihydroxybenzylamino | 52.6/52.9 | 4.3/4.4 | 31.2/30.9 | 273 |
| 2,4-dihydroxybenzylamino | 53.2/52.9 | 4.2/4.4 | 30.6/30.5 | 273 |
| 2-methoxylbenzylamino | 58.1/57.8 | 5.1/5.2 | 30.8/31.1 | 271 |
| 2,3-dimethoxybenzylamino | 55.7/56.0 | 5.3/5.4 | 28.4/28.0 | 301 |
| 3,5-dimethoxy-benzylamino | 56.2/56.0 | 5.5/5.4 | 27.4/28.0 | 301 |
| 2,4,5-trimethoxybenzylamino | 53.8/54.5 | 5.6/5.5 | 25.7/25.4 | 331 |
| 3,4,5-trimethoxybenzylamino | 54.2/54.5 | 5.4/5.5 | 25.7/25.4 | 331 |

Example 8

2-(3-chlorobenzylamino)-6-hydroxypurine 4 mmol of 2-chloro-6-hydroxypurine were dissolved in 20 mL of butanol and then 5 mmol of 3-chlorobenzylamine and 6 mmol of triethylamine were added. The mixture was reacted at 90° C. for 4 hr. After cooling, the product was filter out and washed with water and butanol and crystallized from dimethyformamide or ethanol. HPLC: purity>91%. Yield 88%.

Table 6 compound prepared by the method of example 8

| Compounds prepared by the method of example 8 | | | | |
|---|---|---|---|---|
| | CHN analysis Found/Calculated | | | ESI-MS [M + H⁺] |
| R² substitution | % C | % H | % N | |
| methylamino | 44.1/43.6 | 4.2/4.3 | 42.5/42.4 | 166 |
| ethylamino | 46.7/46.9 | 5.2/5.1 | 39.0/39.1 | 180 |
| propylamino | 49.5/49.7 | 5.6/5.7 | 36.5/36.2 | 194 |
| Isobutylamino | 52.1/52.2 | 6.4/6.3 | 33.7/33.8 | 208 |
| Isopentylamino | 54.2/54.3 | 6.6/6.8 | 31.9/31.7 | 222 |
| hexylamino | 55.8/56.2 | 7.4/7.3 | 30.0/29.8 | 236 |
| cyclopropylamino | 50.7/50.3 | 4.6/4.7 | 36.9/36.6 | 192 |
| cyclobutylamino | 52.1/52.7 | 5.5/5.4 | 34.4/34.1 | 206 |
| cyclopantylamino | 54.1/54.8 | 6.2/6.0 | 32.4/31.9 | 220 |
| cyclohexylamino | 56.1/56.6 | 6.7/6.5 | 29.6/30.0 | 234 |
| anilino | 57.4/58.1 | 4.2/4.0 | 31.1/30.8 | 228 |
| 2-chloroanilino | 50.2/50.5 | 3.2/3.1 | 26.9/26.8 | 263 |
| 3-chloroanilino | 49.8/50.5 | 3.2/3.1 | 27.4/26.8 | 263 |
| 4-chloroanilino | 50.9/50.5 | 3.2/3.1 | 26.4/26.8 | 263 |
| 2-bromoanilino | 43.6/43.2 | 2.4/2.6 | 22.6/22.9 | 307 |
| 3-bromoanilino | 43.5/43.2 | 2.7/2.6 | 22.6/22.9 | 307 |
| 4-bromoanilino | 43.1/43.2 | 2.7/2.6 | 23.1/22.9 | 307 |
| 2-fluoroanilino | 53.5/53.9 | 3.4/3.3 | 28.9/28.6 | 246 |
| 3-fluoroanilino | 54.1/53.9 | 3.4/3.3 | 28.3/28.6 | 246 |
| 4-fluoroanilino | 54.2/53.9 | 3.2/3.3 | 28.8/28.6 | 246 |
| benzylamino | 60.1/59.7 | 4.4/4.6 | 28.7/29.0 | 242 |
| 2-methylbenzylamino | 61.5/61.2 | 5.2/5.1 | 27.1/27.4 | 256 |
| 3-methylbenzylamino | 61.7/61.2 | 4.9/5.1 | 27.2/27.4 | 256 |
| 4-methylbenzylamino | 61.4/61.2 | 5.0/5.1 | 27.3/27.4 | 256 |
| 2-chlorobenzylamino | 51.7/52.3 | 3.9/3.7 | 25.8/25.4 | 277 |
| 3-chlorobenzylamino | 52.9/52.3 | 3.4/3.7 | 25.2/25.4 | 277 |
| 4-chlorobenzylamino | 52.5/52.3 | 3.8/3.7 | 25.3/25.4 | 277 |
| 2-fluorobenzylamino | 55.9/55.6 | 3.6/3.9 | 27.1/27.0 | 260 |
| 3-fluorobenzylamino | 55.1/55.6 | 4.1/3.9 | 27.2/27.0 | 260 |
| 4-fluorobenzylamino | 54.8/55.6 | 4.2/3.9 | 27.5/27.0 | 260 |
| 3-iodobenzylamino | 38.9/39.3 | 2.8/2.7 | 19.3/19.1 | 368 |
| 4-hydroxybenzylamino | 55.8/56.0 | 4.4/4.3 | 27.4/27.2 | 258 |
| 2,3-dihydroxybenzylamino | 52.9/52.7 | 4.3/4.1 | 25.3/25.6 | 274 |
| 3,4-dihydroxybenzylamino | 52.5/52.7 | 4.4/4.1 | 25.8/25.6 | 274 |
| 2,4-dihydroxybenzylamino | 52.1/52.7 | 4.0/4.1 | 25.5/25.6 | 274 |
| 2-methoxylbenzylamino | 57.1/57.6 | 4.9/4.8 | 26.1/25.8 | 272 |
| 2,3-dimethoxybenzylamino | 56.2/55.8 | 4.8/5.0 | 23.1/23.2 | 302 |
| 3,5-dimethoxybenzylamino | 55.1/55.8 | 5.3/5.0 | 23.6/23.2 | 302 |
| 2,4,5-trimethoxybenzylamino | 54.7/54.4 | 5.3/5.2 | 21.0/21.1 | 332 |
| 3,4,5-trimethoxybenzylamino | 54.1/54.4 | 5.4/5.2 | 21.3/21.1 | 332 |

AMPK Activation Assay

Effects of compounds on AMPK activation were analyzed in mouse muscle cell C2C12, mouse fibroblast 3T3-L1 and human hepatocyte Hep G2. Those cell lines were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% CO2. Cells were plated at $3 \times 10^5$ per well (6-well plate). 24 h after plating, cells were treated with indicated compounds for 30 min followed by cell lysis and western blot analysis. Equal amount of protein were separated by SDS-PAGE and then electroblotted on to PVDF membranes. Membranes were blocked with 3% BSA in PBS for 60 min and incubated with anti-phospho-AMPK (Thr172) antibody (1:2,000, Cell signaling), anti-AMPK antibody (1:2,000, Cell signaling), anti-Glut4 antibody (1:1,000, Millipore) or anti-actin antibody (1:5,000; Chemicon International) at 4° C. overnight followed by the corresponding secondary antibody for 1 h at room temperature (RT). Immunoreactive bands were detected by enhanced chemiluminescence (ECL; Pierce, Rockford, Ill., USA) and recorded using Kodakfilm (Rochester, N.Y., USA). The detected signals were scanned and then quantified by using TotalLab Quant software (TotalLab).

The effect of various compounds on AMPK activation is summarized in Table 7. Most of test compounds significantly activated AMPK in C2C12, 3T3-L1 and Hep G2 cells.

TABLE 7

| Agent | Concentration (microM) | AMPK activation (% to control) | | |
|---|---|---|---|---|
| | | C2C12 | 3T3-L1 | Hep G2 |
| 6-hydroxypurine | 1 | 120 | 118 | 114 |
| | 10 | 148 | 155 | 146 |
| | 100 | 233 | 198 | 165 |
| | 200 | 341 | 325 | 330 |
| 2,6-dihydroxypurine | 1 | 105 | 109 | 114 |
| | 10 | 115 | 132 | 139 |
| | 100 | 231 | 205 | 198 |
| | 200 | 347 | 361 | 302 |
| Hypoxanthine | 1 | 108 | 108 | 105 |
| | 10 | 121 | 128 | 124 |
| | 100 | 238 | 231 | 225 |
| | 200 | 309 | 335 | 341 |
| 2-Dimethylamino-6-hydroxypurine | 1 | 105 | 106 | 117 |
| | 10 | 111 | 108 | 132 |
| | 100 | 229 | 205 | 185 |
| | 200 | 298 | 264 | 218 |
| 6-mercaptopurine | 1 | 105 | 114 | 114 |
| | 10 | 119 | 128 | 122 |
| | 100 | 198 | 176 | 204 |
| | 200 | 289 | 218 | 279 |
| 2,6-diaminopurine | 1 | 116 | 108 | 113 |
| | 10 | 181 | 149 | 155 |
| | 100 | 281 | 288 | 274 |
| | 200 | 381 | 335 | 397 |
| 2-hydroxyadenine | 1 | 111 | 117 | 118 |
| | 10 | 166 | 171 | 143 |
| | 100 | 275 | 264 | 220 |
| | 200 | 315 | 351 | 338 |
| Guanine | 1 | 105 | 107 | 119 |
| | 10 | 117 | 121 | 144 |
| | 100 | 241 | 208 | 199 |
| | 200 | 304 | 312 | 335 |
| 6-thioguanine | 1 | 116 | 115 | 116 |
| | 10 | 141 | 132 | 133 |
| | 100 | 215 | 241 | 229 |
| | 200 | 301 | 289 | 311 |
| 2-methyl-6-hydroxypurine | 1 | 109 | 112 | 116 |
| | 10 | 139 | 144 | 162 |
| | 100 | 241 | 228 | 219 |
| | 200 | 305 | 338 | 347 |
| 2-amino-6-mercaptopurine | 1 | 118 | 105 | 112 |
| | 10 | 122 | 119 | 124 |
| | 100 | 228 | 251 | 209 |
| | 200 | 284 | 277 | 261 |
| 2-hydroxy-6-mercaptopurine | 1 | 104 | 118 | 105 |
| | 10 | 109 | 122 | 108 |
| | 100 | 198 | 210 | 204 |
| | 200 | 251 | 277 | 222 |
| 2-amino-6-methylaminopurine | 1 | 119 | 109 | 114 |
| | 10 | 187 | 135 | 139 |
| | 100 | 215 | 220 | 230 |
| | 200 | 351 | 332 | 348 |
| 2-hydroxy-6-methylaminopurine | 1 | 118 | 113 | 115 |
| | 10 | 151 | 162 | 148 |
| | 100 | 255 | 271 | 266 |
| | 200 | 361 | 382 | 354 |
| 2-mercaptoadenine | 1 | 105 | 112 | 118 |
| | 10 | 115 | 128 | 119 |
| | 100 | 221 | 204 | 195 |
| | 200 | 289 | 297 | 308 |
| 2-mercapto-6-hydroxypurine | 1 | 109 | 115 | 113 |
| | 10 | 148 | 147 | 132 |
| | 100 | 251 | 220 | 209 |
| | 200 | 333 | 308 | 315 |
| 2,6-dimercaptopurine | 1 | 104 | 102 | 110 |
| | 10 | 117 | 98 | 133 |
| | 100 | 215 | 178 | 244 |
| | 200 | 298 | 260 | 366 |
| 2-chloroadenine | 1 | 110 | 118 | 116 |
| | 10 | 155 | 143 | 139 |
| | 100 | 284 | 271 | 220 |
| | 200 | 326 | 311 | 314 |
| 2-chloro-6-hydroxypurine | 1 | 109 | 108 | 110 |
| | 10 | 156 | 145 | 163 |
| | 100 | 277 | 243 | 249 |
| | 200 | 331 | 356 | 375 |
| 2-fluoroadenine | 1 | 102 | 114 | 117 |
| | 10 | 112 | 165 | 180 |
| | 100 | 213 | 291 | 259 |
| | 200 | 303 | 323 | 315 |
| 2-bromoadenine | 1 | 116 | 119 | 113 |
| | 10 | 172 | 188 | 190 |
| | 100 | 263 | 277 | 253 |
| | 200 | 349 | 361 | 354 |
| 2-iodoadenine | 1 | 114 | 116 | 115 |
| | 10 | 143 | 179 | 151 |
| | 100 | 214 | 237 | 227 |
| | 200 | 311 | 358 | 341 |
| 2-bromohypoxanthine | 1 | 108 | 111 | 110 |
| | 10 | 142 | 176 | 160 |
| | 100 | 214 | 245 | 242 |
| | 200 | 321 | 357 | 359 |
| 6-methylaminopurine | 1 | 103 | 107 | 116 |
| | 10 | 108 | 129 | 141 |
| | 100 | 213 | 241 | 259 |
| | 200 | 328 | 347 | 363 |
| 6-hexylaminopurine | 1 | 109 | 108 | 112 |
| | 10 | 123 | 111 | 148 |
| | 100 | 248 | 170 | 280 |
| | 200 | 359 | 265 | 317 |
| 6-cyclohexylaminopurine | 1 | 107 | 107 | 111 |
| | 10 | 110 | 152 | 132 |
| | 100 | 248 | 269 | 261 |
| | 200 | 322 | 333 | 354 |
| 6-(4-methylbenzylamino)purine | 1 | 112 | 110 | 106 |
| | 10 | 158 | 163 | 121 |
| | 100 | 270 | 259 | 245 |
| | 200 | 358 | 347 | 348 |
| 6-(3-chloroanilino)purine | 1 | 108 | 116 | 106 |
| | 10 | 118 | 130 | 109 |
| | 100 | 186 | 217 | 212 |
| | 200 | 307 | 301 | 319 |
| 2-amino-6-isopentylaminopurine | 1 | 104 | 110 | 117 |
| | 10 | 114 | 169 | 174 |
| | 100 | 238 | 271 | 250 |
| | 200 | 305 | 361 | 341 |
| 2-amino-6-(2,3-dimethoxybenzylamino)purine | 1 | 106 | 118 | 115 |
| | 10 | 144 | 156 | 127 |
| | 100 | 263 | 250 | 229 |
| | 200 | 334 | 347 | 318 |
| 2-hydroxy-6-propylaminopurine | 1 | 114 | 109 | 110 |
| | 10 | 122 | 129 | 133 |
| | 100 | 201 | 233 | 270 |
| | 200 | 324 | 361 | 339 |
| 2-hydroxy-6-benzylaminopurine | 1 | 108 | 115 | 109 |
| | 10 | 135 | 126 | 137 |
| | 100 | 244 | 230 | 261 |
| | 200 | 356 | 309 | 338 |
| 2-methyl-cyclopentyl-aminopurine | 1 | 105 | 114 | 117 |
| | 10 | 128 | 140 | 140 |
| | 100 | 280 | 241 | 240 |
| | 200 | 342 | 350 | 301 |

TABLE 7-continued

| Agent | Concentration (microM) | AMPK activation (% to control) | | |
|---|---|---|---|---|
| | | C2C12 | 3T3-L1 | Hep G2 |
| 2-methyl-6-(3,4,5-trimethoxybenzylamino)purine | 1 | 106 | 115 | 112 |
| | 10 | 117 | 141 | 168 |
| | 100 | 211 | 254 | 270 |
| | 200 | 361 | 346 | 359 |
| 2-benzylamino-6-aminopurine | 1 | 110 | 119 | 105 |
| | 10 | 128 | 147 | 116 |
| | 100 | 259 | 217 | 235 |
| | 200 | 312 | 308 | 364 |
| 2-cyclohexylamino-6-hydroxypurine | 1 | 108 | 118 | 111 |
| | 10 | 118 | 172 | 137 |
| | 100 | 209 | 283 | 248 |
| | 200 | 321 | 375 | 351 |
| Thymine | 1 | 117 | 109 | 110 |
| | 10 | 147 | 129 | 113 |
| | 100 | 266 | 235 | 218 |
| | 200 | 354 | 318 | 303 |
| Cytosine | 1 | 119 | 117 | 117 |
| | 10 | 158 | 127 | 164 |
| | 100 | 253 | 2436 | 281 |
| | 200 | 361 | 310 | 359 |
| Uracil | 1 | 105 | 114 | 118 |
| | 10 | 109 | 123 | 144 |
| | 100 | 264 | 248 | 237 |
| | 200 | 358 | 372 | 359 |
| 5-methylcytosine | 1 | 116 | 115 | 107 |
| | 10 | 157 | 161 | 114 |
| | 100 | 241 | 253 | 218 |
| | 200 | 338 | 356 | 317 |
| 5,6-dihydrouracil | 1 | 108 | 116 | 120 |
| | 10 | 114 | 159 | 167 |
| | 100 | 207 | 268 | 274 |
| | 200 | 326 | 341 | 360 |
| 5-fluorouracil | 1 | 105 | 108 | 110 |
| | 10 | 105 | 113 | 134 |
| | 100 | 224 | 248 | 237 |
| | 200 | 318 | 322 | 319 |
| Floxuridine | 1 | 117 | 116 | 117 |
| | 10 | 144 | 141 | 147 |
| | 100 | 231 | 222 | 206 |
| | 200 | 312 | 343 | 308 |
| 6-azauracil | 1 | 109 | 109 | 108 |
| | 10 | 109 | 115 | 124 |
| | 100 | 197 | 185 | 199 |
| | 200 | 284 | 288 | 273 |
| AICAR | 1200 | 335 | 340 | 319 |

Glucose Uptake In Vitro

Effects of representative compounds on glucose uptake were analyzed in muscle cell C2C12 by using fluorescent glucose analog (2-NBDG, Molecular Probes). C2C12 were treated with selected novel AMPK activator for 30 min at 37° C. then exposed to 500 μM of fluorescent glucose analog. After 5 min incubation at room temperature, cells were washed three times with Kreb-Hepes buffered solution and fix in 70% alcohol. The fluorescence of glucose analog in cells was detected using a Fluorescence Microplate Reader System at 480-nm excitation and 530-nm emission wavelength.

The effect of selected compounds on glucose uptake is summarized in Table 8 (some data not shown). Most of test compounds significantly stimulated glucose uptake in C2C12 cells. Data are presented as the mean±SEM of three independent experiments.

TABLE 8

| Agent | Concentration (microM) | Glucose uptake (% to control) |
|---|---|---|
| 6-hydroxypurine | 1 | 109 ± 2.2 |
| | 10 | 242 ± 23.7 |
| | 100 | 289 ± 21.4 |
| | 600 | 318 ± 21.2 |
| 6-(4-methylbenzylamino)purine | 1 | 114 ± 9.2 |
| | 10 | 205 ± 14.6 |
| | 100 | 281 ± 11.5 |
| | 600 | 309 ± 9.1 |
| 2-cyclohexylamino-6-hydroxypurine | 1 | 108 ± 2.1 |
| | 10 | 195 ± 11.9 |
| | 100 | 251 ± 16.2 |
| | 600 | 311 ± 10.7 |
| Thymine | 1 | 110 ± 3.2 |
| | 10 | 167 ± 15.1 |
| | 100 | 215 ± 18.2 |
| | 600 | 283 ± 22.3 |
| AICAR | 1200 | 264 ± 19.2 |

In Vivo Assay

To further evaluate the effects of representative compounds on the modulation of plasma glucose level, the high-fat diet-fed mice were served as a type 2 diabetes animal model. C57BL/6J mice were maintained at 22° C. under a 12-h light/dark cycle and fed either a high fat diet (60% kcal % fat) or a normal diet ad libitum. Intraperitoneal injections of selected compounds (0.1 to 50 mg/kg) or vehicle were given to the high-fat diet-fed mice from the age of 24 weeks and glucose readings were measure at 1 and 3 hr. IP administration of the high-fat diet-fed mice continued twice a day for 6 days. On day 6, plasma was collected 1 hr after the last dosing for plasma glucose and triglycerides determined. The select compound were found to decrease plasma glucose >30% and decrease plasma triacylglycerides >35% and decrease body weight >15% relative to control mice.

Disorders such as pre-diabetes, type 2 diabetes, syndrome X, insulin resistance, metabolic syndrome, and obesity may be regulated by activation of AMPK. Thus, specific embodiments and applications of pharmaceutical composition and methods for metabolic modulation have been disclosed. It should be apparent, however, to those skilled in the art that many more modifications besides those already described are possible without departing from inventive concepts herein.

The embodiments are not intended to limit the scope of the present invention. The scope of the present invention is defined only by the appended claims.

What is claimed is:

1. A composition for activating AMPK, comprising an effective amount of at least one compound, tautomers, racemates, optical isomers and/or pharmaceutically or nutritionally acceptable salts thereof, and a pharmaceutical carrier, for administering to a mammal in need of activation of AMPK, wherein the at least one compound is selected from the group consisting of:
   2-benzylamino-6-aminopurine.

2. A method for treating disease or condition susceptible to amelioration by AMPK activators, consisting of administering at least one compound and/or pharmaceutically or nutritionally acceptable salts thereof at a dosage of from 0.1 mg/kg to 50 mg/kg, to a mammal in need of such treatment, wherein increase of glucose uptake into a cell of the mammal and decrease of plasma triglyceride in the mammal are detected and the at least one compound is selected from the group consisting of adenine, 2-benzylamino-6-aminopurine, 2-chloro-6-hydroxypurine, 2-bromoadenine, guanine, hypoxanthine, 5-methylcytosine, thymine, cytosine, uracil, and 5,6-dihydrouracil.

3. The composition of claim 1, wherein the composition is for increasing glucose uptake into a cell and thereby treating a condition selected from the group consisting of pre-diabetes, type 2 diabetes, syndrome X, and metabolic syndrome.

4. The composition of claim 1, wherein the composition is for decreasing plasma triglyceride in mammals and decreasing body weight and thereby treating a condition of obesity.

5. The method of claim 2, wherein administering said at least one compound and/or pharmaceutically or nutritionally acceptable salts thereof to the mammal increases glucose uptake into a cell of the mammal and thereby treating a condition selected from the group consisting of pre-diabetes, type 2 diabetes, syndrome X, and metabolic syndrome.

6. The method of claim 2, wherein administering said at least one compound and/or pharmaceutically or nutritionally acceptable salts thereof to the mammal decreases plasma triglyceride in the mammal and decreases body weight of the mammal, thereby treating a condition of obesity.

\* \* \* \* \*